(12) United States Patent
D'Agostino et al.

(10) Patent No.: US 11,207,545 B2
(45) Date of Patent: Dec. 28, 2021

(54) MASK FOR RADIATION DOSIMETRY

(71) Applicant: SCK.CEN, Brussels (BE)

(72) Inventors: Emiliano D'Agostino, Mol (BE); Luana De Freitas Nascimento, Mol (BE); Filip Vanhavere, Antwerp (BE); Clarita Saldarriaga Vargas, Mol (BE); Marijke De Saint-Hubert, Kessel-Lo (BE)

(73) Assignee: SCK.CEN, Brussels (BE)

( * ) Notice: Subject to any disclaimer, the term of this patent is extended or adjusted under 35 U.S.C. 154(b) by 0 days.

(21) Appl. No.: 15/529,393

(22) PCT Filed: Nov. 25, 2015

(86) PCT No.: PCT/EP2015/077693
§ 371 (c)(1),
(2) Date: May 24, 2017

(87) PCT Pub. No.: WO2016/083473
PCT Pub. Date: Jun. 2, 2016

(65) Prior Publication Data
US 2017/0326387 A1    Nov. 16, 2017

(30) Foreign Application Priority Data
Nov. 25, 2014    (GB) ..................... 1420950

(51) Int. Cl.
*A61N 5/10*    (2006.01)
(52) U.S. Cl.
CPC .... *A61N 5/1071* (2013.01); *A61N 2005/1096* (2013.01); *A61N 2005/1097* (2013.01)

(58) Field of Classification Search
CPC .......... A61N 5/1071; A61N 2005/1096; A61N 2005/1097
See application file for complete search history.

(56) References Cited

U.S. PATENT DOCUMENTS 5,731,590 A    3/1998    Miller
6,316,782 B1    11/2001    Akselrod et al.
(Continued)

FOREIGN PATENT DOCUMENTS

CN    102727239 B    1/2014
EP    2110079 A1    10/2009
(Continued)

OTHER PUBLICATIONS

Great Britain Search Report for corresponding Great Britain Application No. GB 1420950.6, dated May 13, 2015.
(Continued)

*Primary Examiner* — David P Porta
*Assistant Examiner* — Mamadou Faye
(74) *Attorney, Agent, or Firm* — Workman Nydegger (57) ABSTRACT

The present invention describes a membrane mask for immobilization of a region of interest during radiation therapy. The mask comprises at least one material forming a matrix, and at least one radiation-sensitive material integrated as micro- or nano-sized material elements in or onto the matrix. The radiation-sensitive material advantageously provides the possibility of using the mask for performing dosimetry. Use of the mask and a method for performing dosimetry also are described.

17 Claims, 5 Drawing Sheets

(56) References Cited

U.S. PATENT DOCUMENTS

| | | |
|---|---|---|
| 6,846,434 B2 | 1/2005 | Akselrod |
| 7,541,599 B2 | 6/2009 | Moritake et al. |
| 9,452,073 B2 | 9/2016 | Cuypers et al. |
| 2008/0149835 A1 | 6/2008 | Moritake et al. |
| 2009/0114857 A1 | 5/2009 | Demeo et al. |
| 2009/0129556 A1 | 5/2009 | Ahn |
| 2010/0176343 A1 | 7/2010 | Chen et al. |
| 2010/0200741 A1* | 8/2010 | Dotzler .............. C09K 11/7733 250/252.1 |
| 2013/0072839 A1* | 3/2013 | Cuypers .............. A61F 5/05841 602/7 |
| 2013/0218001 A1 | 8/2013 | Uhlemann |
| 2013/0325357 A1* | 12/2013 | Walerow ................. G06F 19/34 702/19 |
| 2014/0264045 A1* | 9/2014 | Marcheschi ............ G01T 1/115 250/368 |

FOREIGN PATENT DOCUMENTS

| | | |
|---|---|---|
| JP | 2002518685 A | 6/2002 |
| JP | 2004309179 A | 11/2004 |
| JP | 2006230510 A | 9/2006 |
| JP | 2007132709 A | 5/2007 |
| JP | 2008538136 A | 10/2008 |
| JP | 2013521904 A | 6/2013 |
| WO | 2006069007 A2 | 6/2006 |
| WO | 2013024380 A1 | 2/2013 |
| WO | 2013167688 A1 | 11/2013 |

OTHER PUBLICATIONS

International Search Report for corresponding International PCT Application No. PCT/EP2015/077693, dated Feb. 4, 2016.

Japanese Office Action from JP Application No. JP2017-528852, dated Oct. 1, 2019.

Osvay et al., "Aluminum Oxide in TL Dosimetry," Nuclear Instruments and Methods, Sep. 31, 1980, 3 Pages.

Colyott et al., "Phototransferred Thermoluminescence in α-Al2O3:C," Radiation Protection Dosimetry, vol. 65, No. 1-4, at least as early as Dec. 31, 1996, p. 263-266.

Cano et al., "TL and EPR in Natural Andalusite Crystal and Application for Gamma-Ray Dosimetry," Encontro de Fisica, at least as early as Dec. 31, 2011, 1 Page.

Kalita et al., "Trap Spectroscopy and Dosimetric Aspects of natural Kyanite Mineral," Applied Physics A, vol. 119, Apr. 5, 2015, pp. 1555-1560.

Office Action from corresponding JP Application No. 2017-528852, dated May 12, 2020.

* cited by examiner

MASK FOR RADIATION DOSIMETRY

FIELD OF THE INVENTION

The invention relates to the field of radiation dosimetry. More specifically it relates to a system for performing two-dimensional dosimetry in radiotherapy

BACKGROUND OF THE INVENTION

Radiation quality control measurements are very important in medical applications like radiotherapy, diagnostic and interventional radiology, etc. In case of radiotherapy, the equilibrium between the necessary dosage for a successful treatment (increasing 'tumor control probability', TCP) and the dosage harming normal tissue (increasing 'normal tissue complication probability', NTCP) is very delicate. It requires the utmost careful and precise control of the applied dose, the area of the radiated region, the number and frequency of doses, the energy of radiation, etc. In this regard, the radiotherapeutic technology has advanced considerably with the aim to deliver higher doses of radiation to the tumor and lower doses to the surrounding tissue. For example intensity-modulated radiotherapy (IMRT) aims to deliver conformal doses to the tumor while minimizing the dose to surrounding normal critical structures. Another example is proton-beam radiotherapy (PRT) which reduces the dose to adjacent normal tissues. Nonetheless the increased complexity of these techniques adds a degree of uncertainties to the delivered dose.

The current clinical protocol to know the delivered dose to the tumor and to the surrounding organs is through the treatment planning systems (TPS) which uses mathematical algorithms. However due to errors in for example positioning of the patient a precise dose calculation does not always correspond to the actual dose delivered to the patient. These errors and other uncertainties, such as radiation scattering, result in the fact that the doses from the TPS do not always provide the accurate doses to the patient. The development of procedures for real-time in vivo dosimetry in radiotherapy forms an important task (IAEA, Human Health Reports No. 8, Vienna 2013). In vivo dosimetry techniques currently involve point source measurements by applying detectors such as for example thermoluminescence detectors (TLDs) or diodes on the skin or immobilization devices of patients. This protocol includes the measurement of entrance and exit doses directly on the patient and to perform a direct quality assurance of radiotherapy. However, this technique was not applicable to IMRT or treatment with very small fields and remains a laborious technique. Moreover, this technique does not deliver two-dimensional information on the dose distribution and its repeatability (positioning the detectors on exactly the same position on the patient) is uncertain.

Due to the fact that most treatments comprise periodical measurements during weeks or months, specific immobilization elements are used in most of the treatment protocols. Examples of these elements include vacuum-lock cushions, "belly boards", and for good reproducibility during a long-term treatment, immobilization molds (perspex shells or other thermoplastic molds). In case of cerebral tumor irradiation for example masks are fixated and molded to enable control of the localization of the provided radiation in subsequent treatments.

SUMMARY OF THE INVENTION

It is an object of embodiments of the present invention to provide a system for performing two-dimensional dosimetry during radiotherapy, and a method of irradiation control on an immobilized object.

The above objective is accomplished by a method and device according to the present invention.

In a first aspect, a radiosensitive material integrated with the materials suitable for immobilization of a volume or region of interest.

In certain embodiments of the present invention, the materials suitable for immobilization may comprise polymers, for example it may comprise a polymeric flexible membrane for advantageous tight application on a volume or region of interest. In this way, masks tightly fitting for example a bodily part can be made, resulting in more accurate immobilization functionality as well as more accurate dosimetry properties. For advantageous immobilization, certain embodiments of the membrane may comprise anchoring features or a frame. In yet further embodiments of the present invention, the polymeric materials may comprise moldable polymeric materials, for example polymers of the group of thermosetting polymers, thermoplastics, or any other material, the present invention not being limited thereto. It is an advantage of embodiments of the present invention that the membrane may form a mold.

The radiosensitive material may be present in the form of small particles, for example microparticles, or nanoparticles, enabling good control of the amount of material added. It is an advantage of embodiments that the final product may keep its properties as an immobilization mask (mechanical properties, color, activation temperature, non-sticking, elasticity, radiation attenuation, etc.). The mixture may be homogeneous, advantageously obtaining good resolution and homogeneous signal.

It is an advantage of embodiments of the present invention that two functionalities are simultaneously combined when using the membrane mask being immobilization of the region of interest and registration and analysis of distribution of doses, both resulting in a good knowledge and eventually in control of the delivered dose.

It is an advantage of embodiments that this mask will serve as immobilization device as well as a reliable, reproducible, and intuitively analyzable dosimeter. It is an additional advantage that the system can perform dose mapping in an accurate and reproducible way, and certain embodiments may advantageously allow mapping in-situ during irradiation.

Certain embodiments of the present invention may further comprise a non-stick surface coating, antibacterial surface coating, or a combination thereof, advantageously reducing peeling and shedding of skin during mask removal, or reducing the risk of infection, or both.

In some embodiments of the present invention, Optically Stimulated Luminescence (OSL) may be used for performing dosimetry. It is an advantage of embodiments of the present invention that reliable and accurate detection, easy to interpret, can be obtained. It furthermore is an advantage that detection of OSL can be performed with not complicated equipment.

In some embodiments of the present invention, Radiophotoluminescence (RPL) may be used for performing dosimetry. It is an advantage of embodiments of the present invention that there may be no signal loss despite any presence of ambient light during manipulation of the mask and during readout of the signal. It is a further advantage of embodiments of the present invention that dose accumulation is possible. Therefore, it is a further advantage that the mask according to certain embodiments of the present invention may be used in sequential irradiation sessions, e.g. in sequential therapeutic sessions.

The polymer can be tailored for optimization of luminescence, for example by choosing the appropriate color according to the desired optical response.

It is an advantage of certain embodiments that a dedicated read-out system can be developed, allowing efficient two-dimensional readout of the skin dose which allows building a dose map of each sequential radiotherapy session. It is an advantage of embodiments of the present invention that dosimetry systems are provided which can be read out in an efficient way.

The membrane mask may have a radio-sensitive layer attached to the mask, i.e. being part of the mask but provided as an outer layer, the radio-sensitive layer comprising between 1% and 90% in weight of radiation-sensitive material.

In another aspect of the present invention, it is provided a method for obtaining a membrane suitable for dosimetry studies, by mixing the powder with a combination of thermoplastic polymers, for example using plastic extrusion, casting, etc., although the present invention is not limited thereto.

Another method included in the present invention for obtaining a membrane suitable for dosimetry studies, is by applying a coating made of a polymeric material mixed with a radiation-sensitive material on the surface of the mask material, by using techniques like roller coating, roller-blade coating, spray coating, etc.; this making the mask equally sensitive to ionizing radiation.

In yet another aspect of the present invention, it is provided a method for performing dosimetry in irradiation procedures. The method comprises applying a mask for immobilizing a region of interest during irradiation of an object, the mask according to embodiments of the first aspect of the present invention. The method further comprises that, during or after irradiation, a physical response is detected of the radiation-sensitive material for estimating thereof a radiation dose applied to the object. The method may comprise detecting a distribution of physical responses of the radiation-sensitive material over the mask surface, advantageously providing information regarding dosage, mapping of the irradiation, for example for estimating the homogeneity of irradiation.

The method may comprise stimulating luminescence from the radiation-sensitive material, using for example optical radiation, the method not being limited thereto. It is an advantage of embodiments that mapping may be performed in situ, during irradiation, in an inexpensive and easy way.

The method according to embodiments of the present invention may further comprise bleaching of stored signal in the mask, advantageously allowing reutilization of the dosimetric qualities of the membrane.

Alternatively, the method may comprise sequential irradiation of the masked region of interest, advantageously allowing a mapping of cumulative irradiation with different irradiation sessions.

In another aspect of the present invention, it is provided the use of a membrane mask according to embodiments of the first aspect of the present invention during irradiation of an object, for advantageously obtaining a map with dosimetry information. In certain embodiments, the use of a membrane mask may be performed sequentially on the same object, for obtaining cumulative dosimetry.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "mask", reference is made to a shaped membrane with such elastic properties that allow tight fixation. The membrane may comprise thermoplastics or other polymers, although the present invention is not limited thereto. Likewise, the term "mask" is not limiting to its use, the mask being applicable to any region, volume or object. The shape of the membrane is advantageously optimized for each particular mask application and advantageously is two-dimensional, following the boundaries of the object around the region of interest. In some embodiments of the present invention, the mask may be suitable for example for immobilization of head, or extremities, or any other part of a body, not being limited thereto, or it may be used for molding, not being limited thereto.

In embodiments of the present invention, the mask comprises one or more radiation-sensitive materials, for example the materials may be embedded in a polymeric matrix, or may be coated on the matrix, although the invention is not limited thereto. By "radiation-sensitive", it is meant that after being exposed to radiation, the materials shows some properties and behavior, which can be measured and depend on the amount of received radiation. These radiation-sensitive materials may advantageously form a homogeneous layer in or on the matrix of the mask, although the present invention is not limited thereto. For instance, it may present a homogeneous layer mainly in the useful surface which shall be utilized, also defined as the region which may cover the region of interest. The sides of the mask may hence be depleted of these materials. The one or more radiation-sensitive materials may comprise luminescent dosimetry material, which may be in form of dosimetry powder embedded in or coated on a matrix, although the present invention is not limited thereto. Where in embodiments of the present invention reference is made to "bleach" or "bleaching", reference is made to the action of erasing the information related to radiation levels stored in the mask.

In a first aspect, the present invention relates to a membrane mask for immobilization of a region of interest during radiation therapy. Immobilization masks typically are used for accurately determining the area of an object, e.g. human or animal body that needs to be irradiated during radiation therapy. By making this immobilization device radiosensitive through derivatization with a radiosensitive material, the mask may serve as a dosimeter. A 3D read-out system may allow constructing a solid map of the administered dose. A further step may incorporate this into the TPS systems to allow an accurate record of the exact delivered dose to the patient. This record could eventually allow to tailor radiotherapeutic doses during sequential sessions of individual patients and achieve optimal treatment (maximize TCP) with minimal side effects (minimize NTCP).

According to embodiments of the present invention, the mask comprises at least one material forming a matrix and at least one radiation-sensitive material integrated as micro- or nano-sized material elements in or on the matrix. Such embedding will allow obtaining a quite homogeneous distribution of the radiation-sensitive material. It is an advantage of embodiments of the present invention that such immobilization masks can be accurately used for dosimetry applications.

In one aspect, the present invention also relates to a method of producing a mask as described in the first aspect. The membranes may be manufactured by, for instance, mixing the dosimetric powder with a combination of thermoplastic polymers (e.g. 1-30% mass concentration of dosimetric powder in mask material) using plastic extrusion, or by applying a polymeric coating mixed with dosimetric material (e.g. 1-30% mass concentration of dosimetric powder in coating material) on the surface of the mask material using roller coating, the present invention not being limited thereto.

Crosslinking of the polymers is conventionally performed by irradiating the material with high radiation doses (e.g. 10 kGy). This requires an extensive bleaching step following production to remove the attained signal. Other crosslinking approaches (e.g. UV crosslinking) would allow omitting these steps and would be desirable for large scale production and applications. In case of coating, this can be applied after the crosslinking, so that no bleaching is needed.

By way of illustration, embodiments of the present invention not being limited thereto, an exemplary mask with standard and optional features will further be described below with reference to the drawings.

The dosimetric material used in a mask according to some embodiments of the present invention may comprise for instance Optically Stimulated Luminescent (OSL) dosimetric material as for example $Al_2O_3$:C microcrystals; or Radio-Photoluminescence (RPL) material as for example $Al_2O_3$:C,Mg microcrystals, although the present invention is not limited thereto.

In embodiments the present invention, 2D maps of radiation entrance dose can be formed on the surface of the mask. Through coupling to the TPS a 3D estimation of the dose in the clinical target volume (CTV) can be performed. It is an advantage of embodiments of the present invention that good resolution and mapping of the irradiated skin region can be obtained without compromising the elastic properties of the mask and without interfering with irradiation treatment plan (e.g. radiation attenuation of the mask). Hence, in advantageous embodiments, the dosimetric powders may comprise particles with a maximum grain size in the range between 5 and 40 μm (micrometers) and a homogenous particle distribution (projected on the mask surface) between, for instance, 10 $\mu g/mm^2$ and 300 $\mu g/mm^2$ for good homogeneity of the measurement. However, the present invention is not limited by these distribution values and particle sizes. The amount of radiation-sensitive material may be selected so that sufficient radiation detection capability is provided and that a sufficient dose range can be reached, but that the properties of the immobilization mask (such as mechanical properties, color, activation temperature, elasticity, radiation attenuation, adhesive factor and others) are maintained within values that do not hinder the utilization of the mask.

Figure 1:
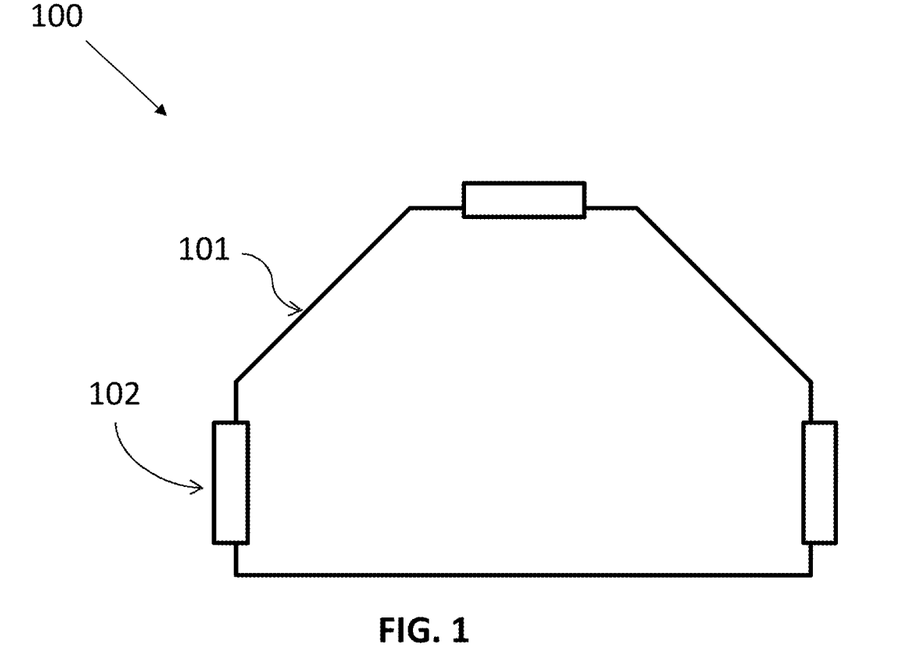
FIG. 1 illustrates a generic mask according to an embodiment of the present invention, comprising anchoring features (102).

The membrane thickness may for example be between 0.5 mm and 3.5 mm, for example between 1.6 mm and 3.4 mm. However, the present invention is not limited by these values. In FIG. 1 there is represented an example of mask 100 comprising a homogeneous material 101 with the dosimetric powder integrated in its matrix (not pictured). In order to provide good immobilization, the mask may further comprise anchoring features 102, which would enable the acquisition of accurate, 3D information of the administered dose by studying the exposition of the mask surface to radiation.

Figure 2:
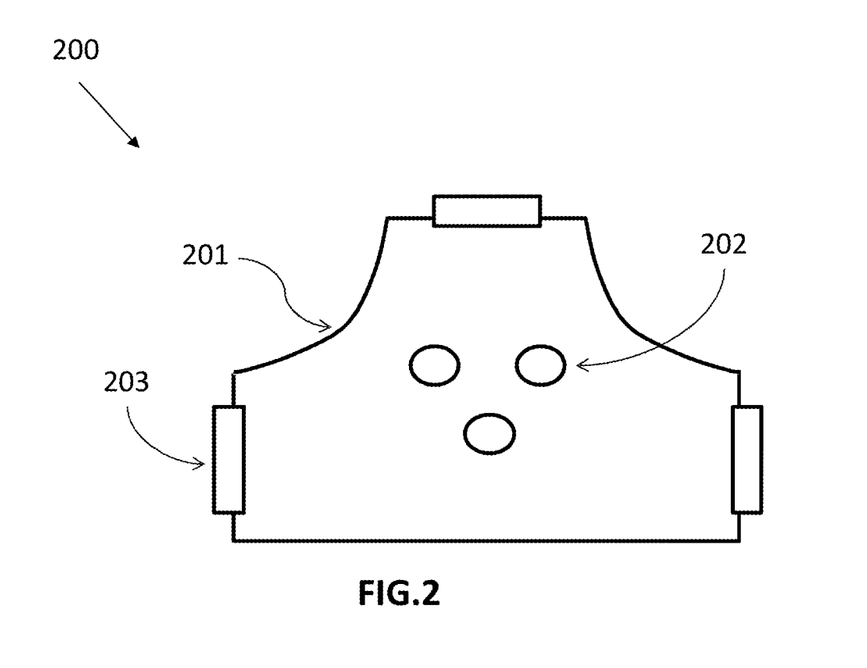
FIG. 2 illustrates an example of a mask according to an embodiment of the present invention suitable for head fixation (202).

The membrane forming the mask may have different shapes, which shall be optimized for each different application. As an example, the embodiment 200 of FIG. 2 shows a perforated mask suitable for facial masks, which may additionally comprise holes 202 for facial features, as eyes, nose or mouth, or a combination thereof, intended to increase comfort of the patient. Other examples may include masks for shoulders, breast, extremities, pelvis, or a combination thereof, not being limited thereof. For instance, the combination of mask for face, neck and shoulders (composed mask) is customary for shoulder retraction.

Figure 3:
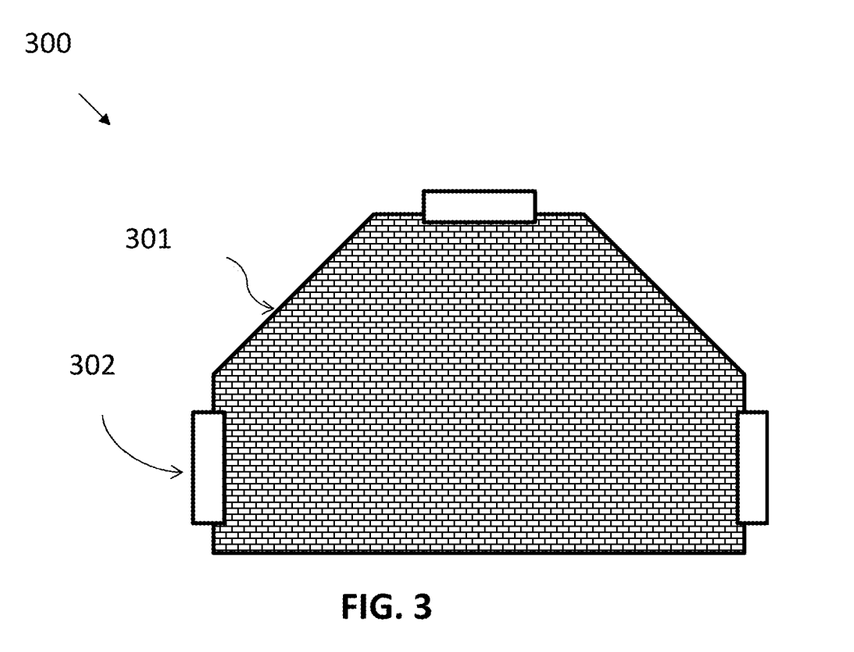
FIG. 3 illustrates an example of a mask according to an embodiment of the present invention comprising at least one layer of mask mesh (301).

In another embodiment 300 schematically shown in FIG. 3, the mask may comprise one or more layers of membrane mesh 301, for instance plastic mesh. If the layers block ventilation, the mask may also comprise as before nose and mouth holes, not shown in the image. Each of the layers of mesh may contain or be coated with luminescent material, or the luminescent material may be mainly comprised in one layer. In one example such a layer may be the surface layer, i.e. the layer furthest to the skin.

The mask matrix may further comprise polymers. For example, it may comprise low density polymers, for minimum interaction with the radiation. For example, the matrix may comprise one or more types of thermoplastics. Hence, their elasticity can be controlled. As an example of one embodiment of the present invention, the matrix may be comprised of a thermoplastic such that the mask can be made soft by applying heat, for instance, and once it is tightly placed on the region of interest, be able to obtain a rigid immobilization mask. Its rigidity would enable reutilization for the same region, hence enabling reproducibility of region position, which is advantageous for long or subsequent treatments. Examples of suitable thermoplastic materials comprise polycaprolactons, or polyurethane, or poly (methil methacrylate) (PMMA), or polyvinyl chloride (PVC) or 1,4-trans-polyisoprene, or a thermoplastic resin (polystyrene, polyethylene), or ethylene vinyl acetate, or polypropilene, or a combination of two or more of them, not being limited thereto. The thermoplastic material may advantageously have low melting temperature, suitable for patient immobilization in, for example but not limited to, radiation oncology applications.

Figure 4:
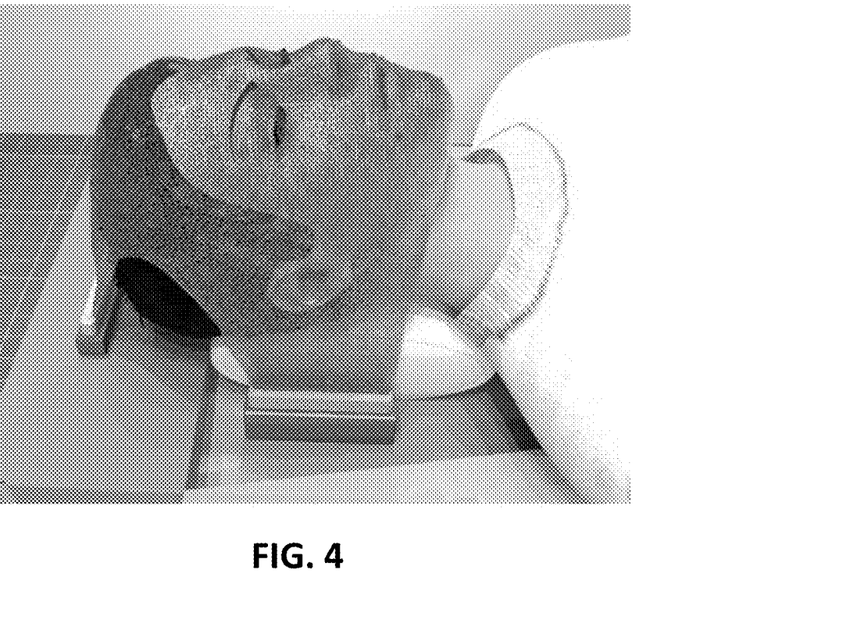
FIG. 4 illustrates a profile view of a mask after fixation and molding, as can be obtained using an embodiment of the present invention.

FIG. 4 shows the side view (or profile) of an immobilization mask after being used as a mold. In this particular example, the composed mask comprises a face mask. The rigidity of the mold allows an accurate dosimetric study of the irradiated regions, together with good immobilization and reproducibility: the same rigid mask can be used for accurately positioning the region of interest in repeated occasions, which is advantageous in the case that further treatment or therapy may be needed.

The mask in different embodiments of the present invention may further comprise a non-stick surface with antibacterial properties, advantageously avoiding interaction with the skin (for example, less shedding of the skin) and reducing the risk of infection in subsequent treatments.

Different embodiments of the present invention are suitable for general immobilization and verification of radiation to the skin of an irradiated region. Through the TPS, the dose to the clinical target volume (CTV) and surrounding organs at risk (OAR) can be calculated. Eventually the device can be used to tailor radiation dose in external therapy, radiotherapy, brachytherapy, internal radiotherapy, or stereotactic radiosurgery (SRS). The benefits of immobilization in radiation therapy are well known (for instance, reduction of damage in healthy tissue during a therapy session). Additionally, the present invention allows more precise control of the entire therapy procedure and dosage. Generally, in radiation therapy, each treatment requires a determined amount of radiation. For example, in case of Hodgkin lymphoma, the applied total radiation dosage ranges between 20 and 40 Gy. The human is very sensitive to radiation and such high doses may be lethal, so the dosage is fractioned, for example in doses of less than 2 Gy during several weeks. The present invention provides with a device which enables a precise measurement of the amount of radiation dose received during sequential therapy sessions, as well as information regarding the surface of irradiated region, by studying the radiation exposure of the immobilization mask. Thus, corrections of intensity and irradiated surface (for instance, reducing the irradiated surface so nearby tissue is not harmed) can be performed in early stages of the treatment, improving quality control. The invention can also lead to early detection of misalignment or instrument malfunctions, thus preventing over- or underexposure accidents in radiotherapy.

In one aspect, the present invention relates to a method for performing dosimetry, the method comprising applying a mask for immobilizing a region of interest during radiation therapy or radiation of an object, the mask comprising a material forming a matrix with at least one radiation-sensitive material embedded as micro- or nanosized material element therein, or with at least one radiation-sensitive material coated upon it, and during or after radiation therapy, detecting a physical response of the radiation-sensitive material for estimating thereof a radiation dose. The method can assist for estimating a distribution of radiation doses in the object that was subject to the radiation therapy based on a distribution of the physical responses of the radiation-sensitive material over the surface of the mask. The method consequently also may comprise detecting a distribution of physical responses of the radiation-sensitive material over the mask surface. Detection of the physical response may comprise stimulating luminescence from the radiation-sensitive material, using for example optical radiation.

By way of illustration some examples will be further discussed below.

The steps for obtaining the information from the mask for specific examples are presented. First, the dosimetric material needs to be mixed with the mask material. Alternatively, the dosimetric material can be mixed with a suitable coating material that is then applied on the surface of the mask. This can be done before the mask is shaped according the object, but the invention is not limited to this. The mask, being the immobilizing means for the region of interest, is irradiated together with the region of interest. The integrated radiation-sensitive material, e.g. powder (for instance, luminescent powder) is hence irradiated, due to the exposure of the mask to radiation. The radiation energy is partially stored by the radiation-sensitive material only in those regions exposed to radiation. Then, during or after irradiation, the energy stored in the powder crystals can be released e.g. in form of light, e.g. by inducing the release using a stimulation step, which can be collected by detectors and analyzed. An accurate mapping of the amount of radiation is then obtained. This information can be used to assess the dose received in the CTV and/or estimate the effective irradiated volume. It is an advantage that e.g. using irradiation modelling, a two-dimensional or even three-dimensional (3D) dosage estimation can be made for the radiation therapy performed. With such 3D dose estimation, a feedback to the TPS can be organized to compare with the planned doses, and to optimize further treatments.

The measurement of the dose of radiation absorbed by the membrane depends on the type of radiation-sensitive material introduced in the matrix of the mask or in the coating on the matrix. Some mechanisms shall be further explained in more detail, underlining the differences in measurement technique and principles.

First, in case of masks comprising OSL dosimetric powder, the radiation excites the electrons in the valence band of the crystalline structure of the microcrystals forming the powder. The energy may be high enough to produce ionization, so the electrons overcome the relatively wide bandgap of luminescent materials, which creates electron-hole pairs. The excited electrons, now in the conduction band, may recombine with holes again or become trapped in crystal defects, which act as electron traps. Recombination centers can trap both holes and electrons. In case of OSL dosimetric $Al_2O_3$:C crystals, the typical crystal defects acting as recombination centers are usually oxygen vacancies (but other crystals may admit other types of recombination centers). Hence, electrons and holes remain trapped in the recombination center in an amount equal to the amount of received radiation, and the energy is stored. When the crystal is stimulated with enough energy, the electrons trapped in the defect overcome the energy barrier and recombine with the holes, producing luminescence. In case of the oxygen recombination centers, this energy is close to 420 nm, hence within the visible spectrum. The stimulation is produced by exposing the mask to green or blue light, creating luminescence in the material. This luminescence has a starting peak $P_{OSL}$ and decreases with time, because recombination centers are being depleted of electron-hole pairs. This information ($P_{OSL}$ and integration of the total curve $T_{OSL}$) can be used to calculate the amount of electron-hole pairs (and hence, the amount of radiation) received by the mask. Other OSL materials can have different specifications.

The stimulation signal can be continuous (Continuous Wave OSL or CWOSL), pulsed OSL, etc. In case of FIGS. 5 and 6, the studies were performed on an OSL dosimetry mask using a membrane containing 3% in mass of $Al_2O_3$:C powder, and the stimulation was performed with CWOSL. The OSL measurement may be performed with a blue stimulation light source (for instance, 470 nm) and a photomultiplier tube with a blue filter to collect the luminescence signal. Other methods for detecting the emitted light are also possible.

Figure 5:
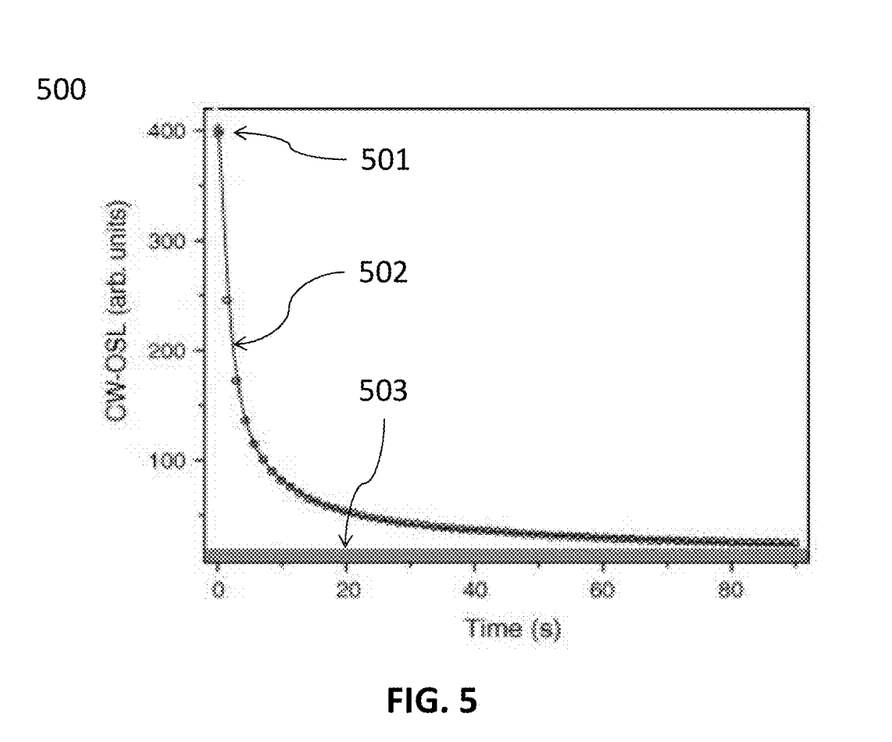
FIG. 5 illustrates a graph of the depletion of electron-hole pairs during continuous OSL stimulation, as can be used in embodiments of the present invention.

FIG. 5 shows a graph 500 with the typical behavior of electron depletion in the traps, under continuous illumination. The peak $P_{OSL}$ is the point 501, the total curve $T_{OSL}$ 502 is represented and, due to the polymeric matrix, there is a background 503, which is necessary to take into account.

Figure 6:
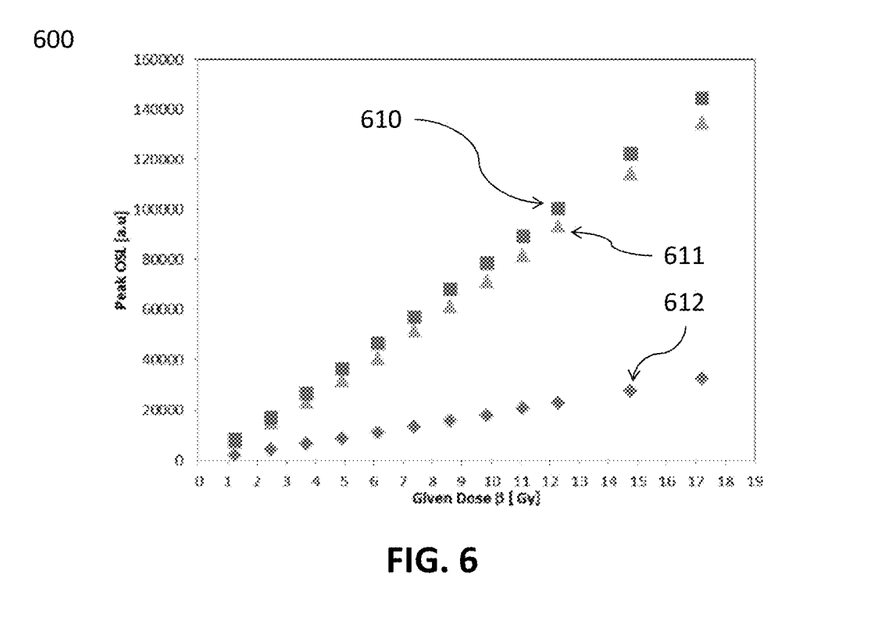
FIG. 6 illustrates a graph of the different responses of OSL masks containing different polymeric matrices, according to composition and color, to stimulation, illustrating advantages of embodiments of the present invention.

Not only the type of polymeric matrix, but even its color may have an influence in the absorption/emission of light. The depletion curve may also depend on the type of matrix. FIG. 6 shows a graph 600 with a comparison of different $P_{OSL}$ for three different polymeric matrices' colors (yellow 610, green 611, and blue 612), for different dosages using a beta-source $^{90}Sr/^{90}Ir$.

Figure 7:
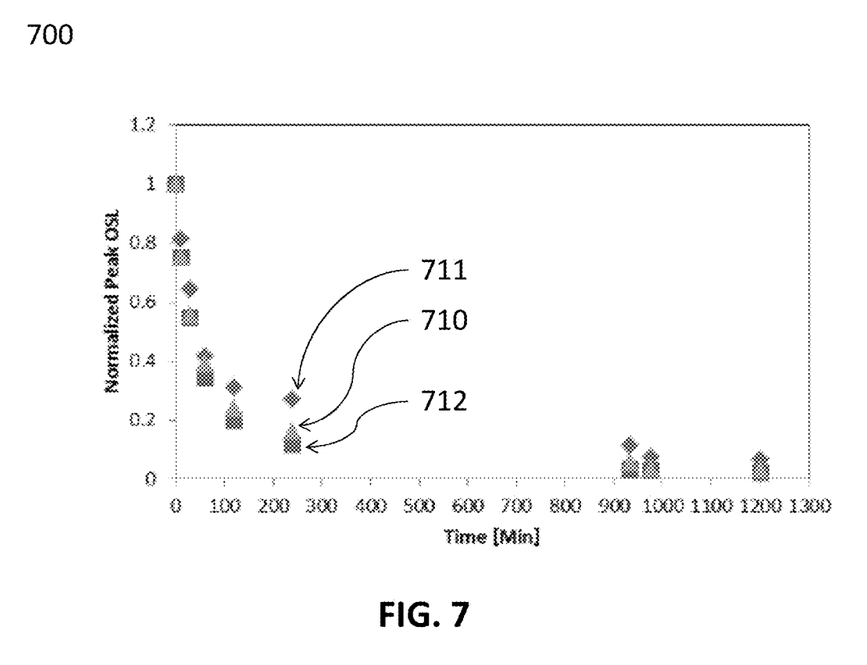
FIG. 7 illustrates a graph of different responses of OSL masks containing different polymeric matrices, according to composition and color, to ambient light, illustrating advantages of embodiments of the present invention.

Due to the fact that electrons recombine under excitation (stimulation) with light, the ambient light may affect the results if masks are exposed to light before the reading. FIG. 7 shows a graph 700 with different responses for different exposures of ambient light, for the same polymeric matrices as before (yellow 710, green 711, and blue 712).

Secondly, in case of masks with integrated RPL dosimetric powder, the crystals may comprise $Al_2O_3$ doped with Carbon and Magnesium ($Al_2O_3$:C,Mg), although the present invention is not limited thereto. The underlying mechanism for $Al_2O_3$:C,Mg relies on radiochromic transformations of the luminescent centres following exposure to ionizing radiation. Upon exposure to ionizing radiation, electrons in the valence band are ionized and then are trapped in $F_2^{2+}$ (2 Mg) photoluminescent centers, which follow a radiochromic transformation as follows:

$$F_2^{2+}(2Mg)+e^- \rightarrow F_2^+(2Mg)$$

The concentration of $F_2^+$ centers is proportional to the irradiation dosage, which can be read using 250, 335 or 620 nm light. The stimulation of the $F_2^+$ centers results in emission of RPL at 750 nm which is proportional to the irradiation dose. Interestingly, the stimulation (reading) of the stored energy does not destroy the centers, unlike OSL. Therefore the stored dose can be read-out in between irradiations and cumulated over several irradiations.

In order to erase (bleach) the stored information it is necessary to use high power 335 nm light (e.g. $N_2$ laser 337 nm), according to:

Following bleaching the material can be re-used and, for example, it can measure the dose in another radiotherapy session. Even without bleaching, the accumulated dose can be continued to be measured. The advantage of RPL over OSL is the lack of loss of stored information (RPL signal) under ambient light, and the non-destructive read-out. Hence it is possible to track the accumulated received dosage (cumulative dose). The reading may be performed using for example a red stimulation light (620 nm), for instance using LEDs, and a photomultiplier equipped with appropriate optical filters. In case of FIGS. 8 and 9, the studies were performed on an RPL dosimetry mask containing 3-5 mass % of $Al_2O_3$:C,Mg.

Figure 8:
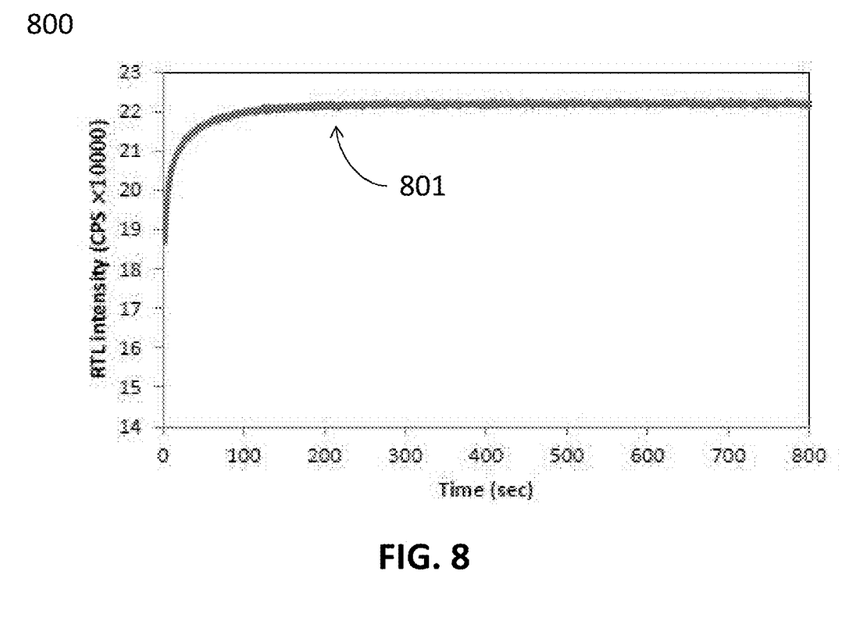
FIG. 8 illustrates a graph with a typical RPL readout in an RPL mask after irradiation with gamma irradiation, illustrating advantages of embodiments of the present invention.

FIG. 8 shows a graph 800 with the typical RPL readout 801 in an RPL mask (3% in mass of $Al_2O_3$:C,Mg) after being irradiated with gamma radiation. The stimulation was performed with a continuous-wave red light (620 nm). The average RPL signal is then calculated.

Figure 9:
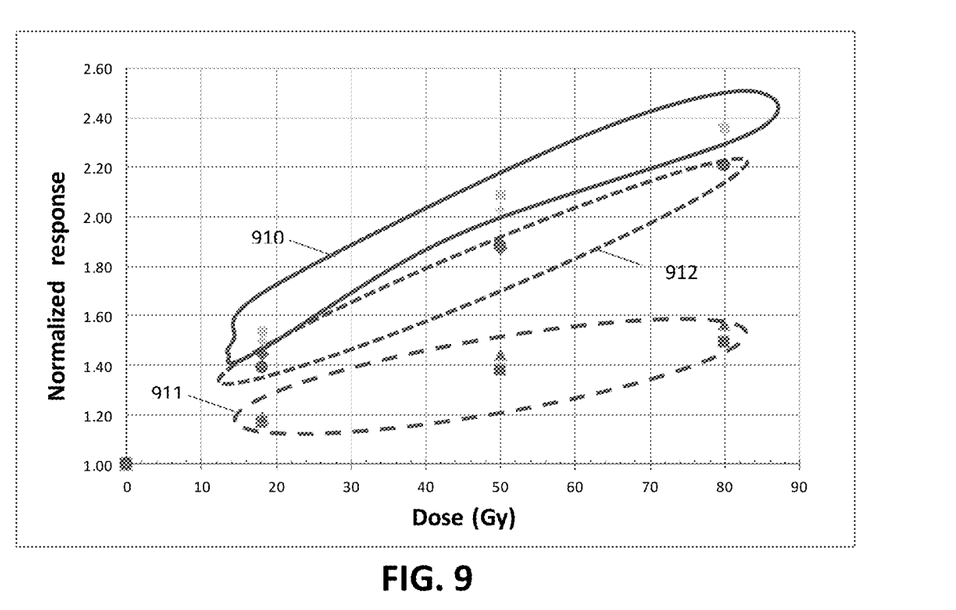
FIG. 9 illustrates the RPL responses to different irradiation doses of yellow, blue and green polymeric mask materials mixed with Al2O3: C,Mg dosimetric powder (values normalized to the RPL response at 0 Gy), illustrating advantages of embodiments of the present invention.

As before, the type of polymeric matrix and its color may affect the measurements. FIG. 9 shows average RPL signal normalized to the zero-dose (0 Gy) average RPL for yellow 910, green 911 and blue 912 polymer (5% in mass of $Al_2O_3$:C,Mg) for given doses (18 Gy, 50 Gy and 80 Gy) of beta radiation ($^{90}Sr/^{90}Ir$). A positive dose-response is observed for each of the polymers. As it can be seen in the graph the yellow polymer 910 is more sensitive compared to the blue 912 and green polymer 911.

Figure 10:
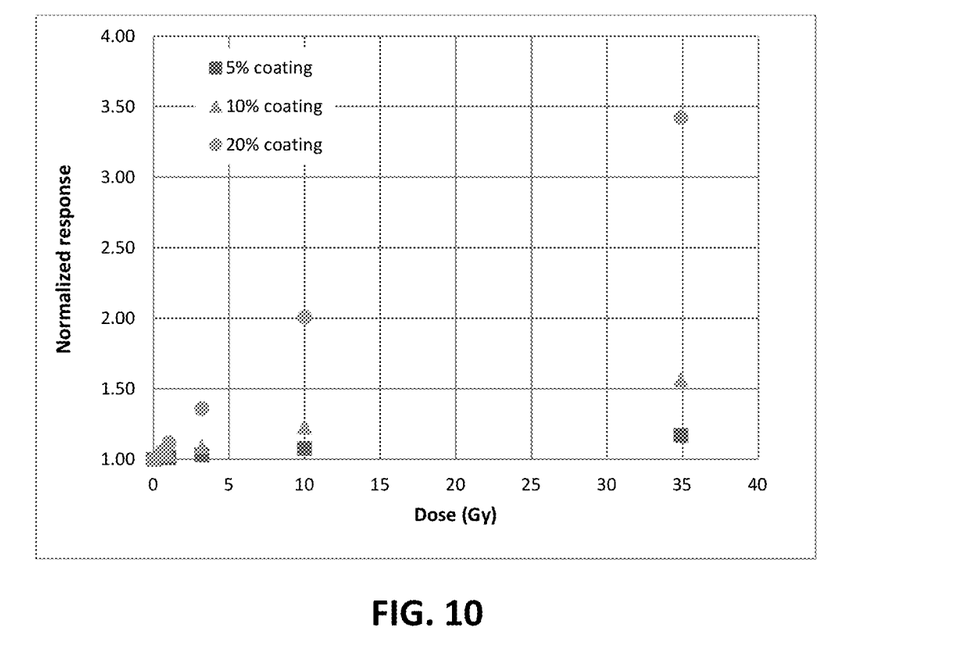
FIG. 10 illustrates the RPL response to different irradiation doses of mask material with dosimetric coatings of different Al2O3: C,Mg concentrations (5, 10 and 20%) (values normalized to the RPL response at 0 Gy), illustrating advantages of embodiments of the present invention.

As mentioned before, the radiation-sensitive material can be integrated to the mask material by, for instance, applying a coating made of a polymer material mixed with dosimetric powder on the surface of the matrix. FIG. 10 illustrates the RPL signal normalized to the zero-dose (0 Gy) average RPL of yellow mask material coated with a dosimetric coating containing different concentrations of $Al_2O_3$:C,Mg powder (5, 10 and 20% mass concentration of $Al_2O_3$:C,Mg in coating material), for different doses (0.6 Gy, 1.0 Gy, 3.2 Gy, 10.0 Gy and 34.9 Gy) of beta radiation ($^{90}Sr/^{90}Ir$). There it can be seen that the RPL signal increases with the amount of radiation received by the coated sample and also with the concentration of powder in the coating.

In certain embodiments, radiation control may be performed in situ during radiation therapy by monitoring dosimetry of the mask. This would be possible by performing the stimulation of the physical effect during radiation therapy, instead of removing the mask before stimulating the luminescence. This would require the development of a dedicated reader that does not interfere with the radiation therapy itself.

It is to be noticed that the step of irradiating the object in the radiation therapy is not part of the present invention as such. The present invention relates to a dosimetry method and the dosimetry is performed by measuring a physical effect of an immobilization mask, which does not require measurement of a physical effect in the human or animal body. Consequently, the method does not require interaction with the human or animal body and is not a method of surgery or a method of therapy.

The invention claimed is:

1. A membrane mask for immobilization of a region of interest during radiation therapy, the mask comprising:
   at least one material forming a matrix, and
   at least one radiation-sensitive material integrated as micro- or nano-sized material elements in or onto the matrix;
   wherein the at least one radiation-sensitive material is configured for use in luminescence dosimetry;
   wherein the at least one radiation-sensitive material is configured to store radiation energy and to release the radiation energy in the form of light.

2. The membrane mask according to claim 1, wherein the radiation-sensitive material comprises powdered materials.

3. The membrane mask according to claim 1, wherein the micro- or nano-sized material elements are substantially homogeneously dispersed in or onto the matrix on at least a part of a useful surface area of the membrane mask.

4. The membrane mask according to claim 1, wherein the micro- or nano-sized material elements have a maximum grain size between 5 and 40 micrometers.

5. The membrane mask according to claim 1, wherein the radiation-sensitive material is luminescent material sensitive for Optically Stimulated Luminescence (OSL) or Radio Photoluminescence (RPL).

6. The membrane mask according to claim 1, wherein the mask or a coating on the membrane mask comprises between 1% and 30% by weight of radiation-sensitive material.

7. The membrane mask according to claim 1, wherein a radio-sensitive layer is attached to the membrane mask comprising between 1% and 90% in weight of radiation-sensitive material.

8. The membrane mask according to claim 1, wherein the material forming the matrix comprises at least one layer of polymeric material and/or wherein the material forming the matrix is a moldable material.

9. The membrane mask according to claim 1, wherein the membrane mask further comprises anchoring features.

10. The membrane mask according to claim 1, wherein the membrane mask further comprises a non-stick surface coating and/or an antibacterial surface coating.

11. A method for performing dosimetry, the method comprising:
   applying a mask for immobilizing a region of interest during irradiation of an object, the mask comprising a material forming a matrix with at least one radiation-sensitive material embedded as micro- or nano-sized material elements therein or thereon; and
   during or after irradiation, detecting a physical response of the radiation-sensitive material for estimating therefrom a radiation dose applied to the object;
   wherein the at least one radiation-sensitive material is configured for use in luminescence dosimetry;
   wherein the at least one radiation-sensitive material is configured to store radiation energy and to release the radiation energy in the form of light.

12. The method according to claim 11, wherein said detecting comprises detecting a distribution of physical responses of the radiation-sensitive material over a surface of the mask.

13. The method according to claim 11, wherein said detecting comprises stimulating luminescence from the radiation-sensitive material, using for example optical radiation.

14. Use of a membrane mask according to claim 1 during irradiation of an object for obtaining dosimetry information.

15. Use of a membrane mask according to claim 1 during sequential irradiation of the same object for obtaining dosimetry information.

16. A membrane mask for immobilization of a region of interest during radiation therapy, the mask comprising:
- at least one material forming a matrix; and
- at least one radiation-sensitive material integrated as micro- or nano-sized material elements in or onto the matrix, wherein the radiation-sensitive material shows measurable properties and behavior upon interaction with the radiation;
- wherein the at least one radiation-sensitive material is a doped aluminum oxide;
- wherein the at least one radiation-sensitive material is configured for use in luminescence dosimetry;
- wherein the at least one radiation-sensitive material is configured to store radiation energy and to release the radiation energy in the form of light.

17. The membrane mask according to claim 1, wherein a radio-sensitive layer is attached to the membrane mask comprising 20% in weight of the radiation-sensitive material.

* * * * *